US00PP28393P3

(12) United States Plant Patent
Alkemade

(10) Patent No.: US PP28,393 P3
(45) Date of Patent: Sep. 12, 2017

(54) ***SALVIA* PLANT NAMED 'ALKLF'**

(50) Latin Name: *Salvia nemorosa*
Varietal Denomination: ALKLF

(71) Applicant: Theo Alkemade, Lisse (NL)

(72) Inventor: Theo Alkemade, Lisse (NL)

( * ) Notice: Subject to any disclaimer, the term of this patent is extended or adjusted under 35 U.S.C. 154(b) by 5 days.

(21) Appl. No.: 14/757,332

(22) Filed: Dec. 17, 2015

(65) Prior Publication Data

US 2017/0208729 P1 Jul. 20, 2017

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Penny J. Aguirre

(57) ABSTRACT

A new cultivar of hybrid *Salvia*, 'ALKLF', that is characterized by its dwarf plant habit, its numerous racemes of blue-violet flowers, its sterility, and its abundance of shoots produced after one pinch.

2 Drawing Sheets

Botanical classification: *Salvia nemorosa.*
Variety denomination: 'ALKLF'.

BACKGROUND OF THE INVENTION

The present invention relates to a new and distinct cultivar of *Salvia nemorosa* and will be referred to hereafter by its cultivar name, 'ALKLF'. 'ALKLF' is an herbaceous perennial grown for landscape use.

The Inventor discovered 'ALKLF' in 2013 in a production field planted with 6,000 plants of *Salvia nemerosa* 'Ostfriesland' (not patented) derived from vegetative propagation in Lisse, The Netherlands. 'ALKLF' therefore derived as a naturally occurring chimeral mutation of 'Ostfriesland'.

Asexual reproduction of the new cultivar was first accomplished by the Inventor by vegetative stem cuttings in 2013 in Lisse, The Netherlands. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'ALKLF' as a unique cultivar of *Salvia.*

1. 'ALKLF' exhibits a dwarf plant habit.
2. 'ALKLF' exhibits numerous racemes of blue-violet flowers.
3. 'ALKLF' exhibits many shoots after one pinch.

'Ostfriesland', the parent of 'ALKLF', differs from 'ALKLF' in having a larger plant size (50 to 60 cm in height), in having a plant habit that is not dwarf and in having less shoots after one pinch. 'ALKLF' can be compared to the cultivars 'Haeumanarc' (U.S. Plant Pat. No. 13,322), 'Pink Friesland' (U.S. Plant Pat. No. 18,152), and 'Burgundy Candles' (U.S. Plant Pat. No. 22,754), 'Haeumanarc' differs from 'ALKLF' in having an even more dwarf plant habit and in having inflorescences that are shorter in length. 'Pink Friesland' differs from 'ALKLF' in having a much taller plant habit and in having pink flowers. 'Burgundy Candles' differs from 'ALKLF' in having a much taller plant habit and in having burgundy colored flower bracts.

BRIEF DESCRIPTION OF THE DRAWING

The accompanying colored photographs illustrate the overall appearance and distinct characteristics of a 3 month-old plant (from a rooted cutting) of the new *Salvia* as grown in a two-liter container in Lisse, The Netherlands.

The photograph in FIG. 1 provides a view of 'ALKLF' in bloom.

Figure 1:
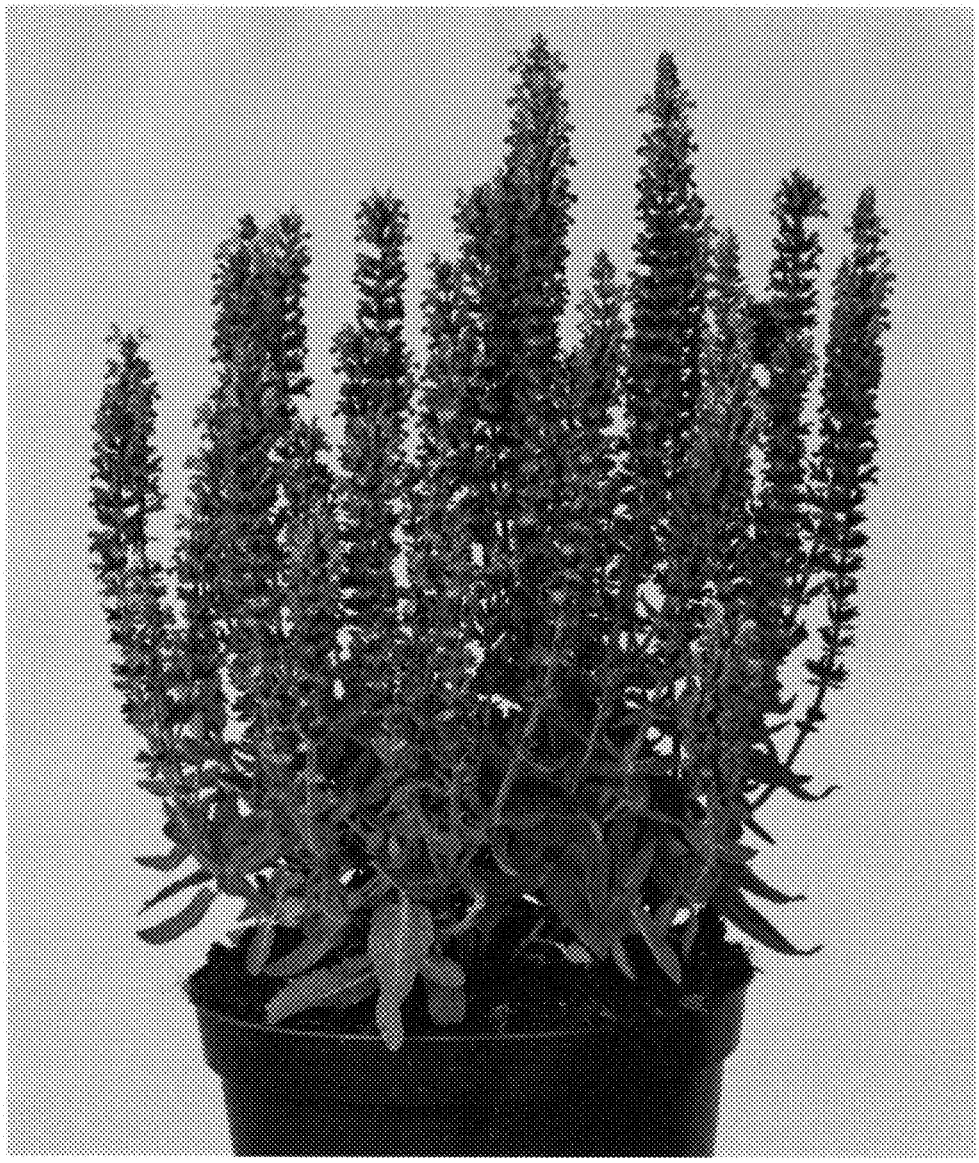
Figure 2:
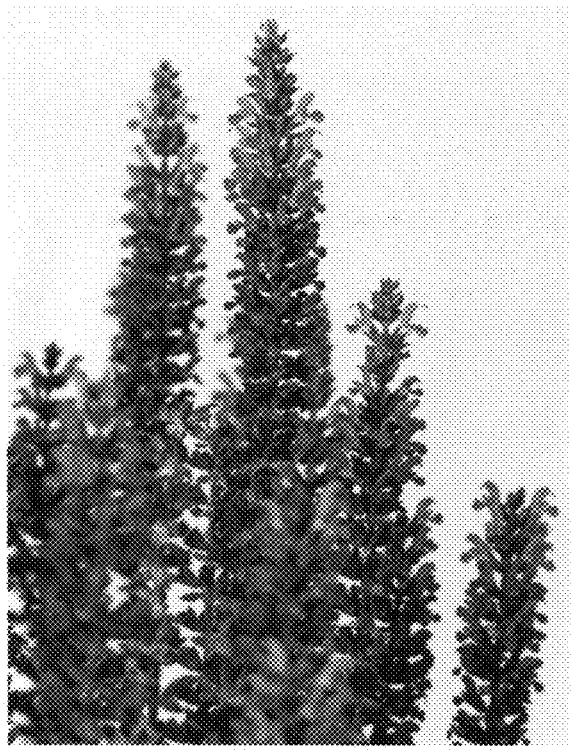

The photograph in FIG. 2 provides a close-up view of an inflorescence of 'ALKLF'.

Figure 3:
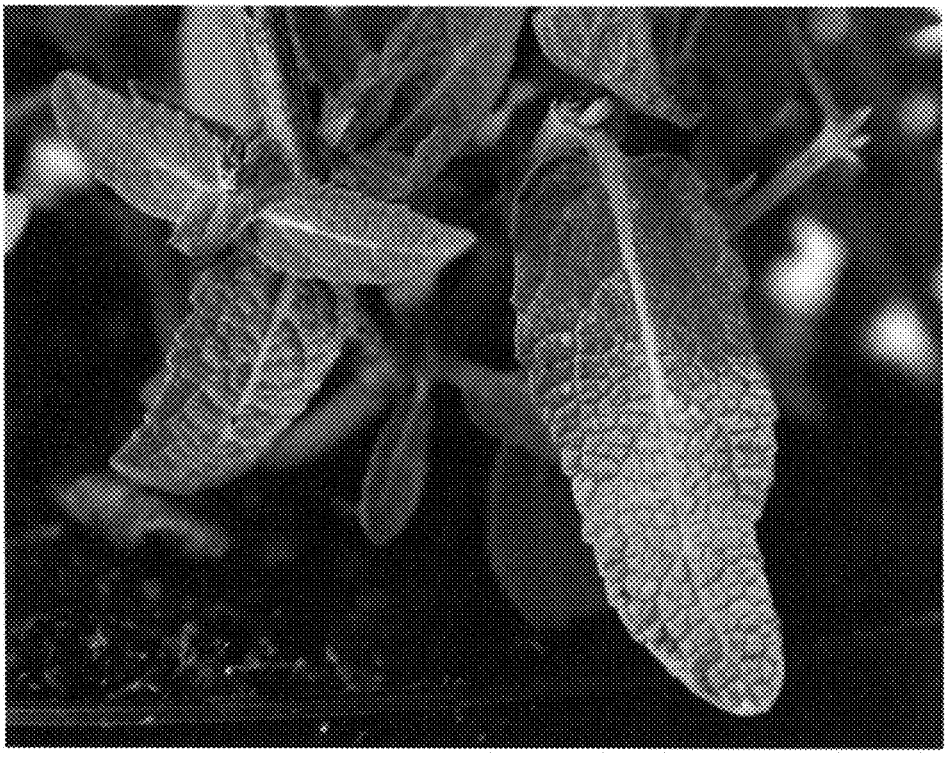

The photograph in FIG. 3 provides a close-up view of the foliage of 'ALKLF'.

The colors in the photographs may differ slightly from the color values cited in the detailed botanical description, which accurately describe the colors of the new *Salvia.*

DETAILED BOTANICAL DESCRIPTION

The following is a detailed description of the new cultivar of plants 3 months in age (from a rooted cutting) as grown outdoors in 2-liter containers in Lisse, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Spring to summer in The Netherlands.

*Plant type.*—Herbaceous perennial.

*Plant habit.*—Broad upright, dwarf.

*Plant size.*—Average of 28.2 cm in height and 25.8 cm in diameter.

*Cold hardiness.*—At least tolerant to U.S.D.A. Zone 4.

*Diseases and pests*.—No susceptibility or resistance to diseases or pests has been observed.

*Root description*.—Fibrous and fine and 155C in color.

*Root development*.—About 10 days to initiate roots and 30 days to produce a young rooted plant.

*Propagation*.—Stem cuttings.

*Growth rate*.—Moderately vigorous.

Stem description:

*Shape*.—Quadrangular.

*Stem color*.—138B.

*Stem size*.—Average of 6.2 cm in length and 2 mm in width.

*Stem surface*.—Matte and densely covered with very short soft hairs, average of 0.2 mm in length and too small to measure color.

*Stem aspect*.—Held at an average angle of 30° to main branches.

*Internode length*.—Average of 1.9 cm in length.

*Branching*.—Average of 26 branches (after a single pinch).

*Stem fragrance*.—Stems have a typical "sage" fragrance when rubbed.

Foliage description:

*Leaf shape*.—Narrow ovate to narrow oblong.

*Leaf division*.—Simple.

*Leaf base*.—Truncate to obtuse.

*Leaf apex*.—Obtuse.

*Leaf fragrance*.—Leaves have a typical "sage" fragrance when rubbed.

*Leaf venation*.—Pinnate, upper surface color 147D, lower surface color 144A.

*Leaf margins*.—Shallow crenate.

*Leaf arrangement*.—Opposite.

*Leaf attachment*.—Petiolate.

*Leaf surface*.—Moderately rugose, upper side slightly very glossy and glabrous, lower side matte and densely covered with very short glandular hairs; an average of 0.2 mm in length and too small to measure color.

*Leaf size*.—Up to 3.8 cm in length and 1.6 cm in width.

*Leaf color*.—Young upper surface; NN137B, young lower surface; 147B, mature upper surface; NN137A, mature lower surface; 147B.

*Petioles*.—Average of 6 mm in length, petiole flattened, average diameter at widest point 2.75 mm, average diameter at narrowest point 1.5 mm, 144B to 144C in color, pubescent surface.

Inflorescence description:

*Inflorescence type*.—Terminal raceme of bilabiate flowers.

*Lastingness of inflorescence*.—Individual flowers average of 5 days.

*Inflorescence size*.—An average of 16.5 cm in length and 1.8 cm in width.

*Flower type*.—Bilabiate.

*Flower aspect*.—Outward.

*Flower number*.—Average of 140 per vertillicaster (individual flowers in whorls, average number of flowers per whorl 6).

*Flower fragrance*.—None.

*Flower buds*.—Obovate in shape, about 5 mm in length and 2 mm in diameter, 143C, top N89B to N89C.

*Flower size*.—Average of 4.5 mm in width and 8 mm in height.

*Peduncle*.—An average of 16 cm in length and 1.5 mm in width, color; 138B, tinged N186B, held straight on top of lateral branch, strong in strength, pubescent surface.

*Pedicels*.—Average of 1.5 mm in length, 0.75 mm in diameter, color; N77C, held at an average angle of 20° (0°=straight upright), strong in strength, pubescent surface.

*Calyx*.—Campanulate in shape, average of 4.5 mm in length and 2 mm in diameter, 3 mm in height.

*Sepals*.—5, base is cuneate and fused 55%, narrow obovate in shape, entire margin, acute apex, campanulate arrangement, both surfaces are dull with very short glandular hairs; an average of 0.01 mm in length and too small to measure color, average of 4.5 mm in length and 1.5 mm in width, color; immature upper side 145B, tinged N77B, immature lower side 143C, tinged N77C at the top, mature upper side 145A, tinged N77B, mature lower side 146B, tinged N77C.

*Petals*.—2, fused at base 50%, labiate, upper lip; broad elliptic, folded in shape, margin entire, apex obtuse, 9 mm in length and 1.5 mm in width, based fused, lower lip; broad hastate in shape, margin entire, apex obtuse, 8 mm in length and 4.5 mm in width, base fused, color of upper and lower lip; when opening upper and lower side N88A with base N155A, when fully open upper and lower side N89C with base N155A, petal color fading on all surfaces to N88A and N89B.

*Bracts*.—2 present under each whorl of 6 individual flowers, orbicular in shape, abruptly acute apex, broad cuneate base, average of 5 mm in length and width, color; NN74C to NN74D, veined 147B, surface glabrous with margins pubescent.

Reproductive organs:

*Gynoecium*.—Pistil; 1, 8 mm in length, style; 9 mm in length, N80D in color, stigma; cleft (2 parted), 9 mm in length and N88A in color, ovary; superior, oblong in shape, about 3 mm in length, and 144A in color.

*Androcoecium*.—2 stamens, filaments; N155A in color, 2 mm in length, anthers; dorsifixed, narrow elliptic in shape, 0.05 mm in length, N199D in color, pollen; low in quantity and 11D in color.

*Fruit and seed*.—None have been observed to date.

It is claimed:

1. A new and distinct cultivar of *Salvia* plant named 'ALKLF' as herein illustrated and described.

* * * * *